(12) United States Patent
Vogt

(10) Patent No.: US 9,415,134 B2
(45) Date of Patent: Aug. 16, 2016

(54) FOSFOMYCIN PREPARATION, A METHOD FOR PRODUCING THE PREPARATION, AND A POLYMETHYLMETHACRYLATE BONE CEMENT POWDER CONTAINING THE PREPARATION

(71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 14/673,922

(22) Filed: Mar. 31, 2015

(65) Prior Publication Data
US 2015/0283291 A1 Oct. 8, 2015

(30) Foreign Application Priority Data

Apr. 2, 2014 (DE) .......................... 10 2014 104 676

(51) Int. Cl.
| | | |
|---|---|---|
| *A61K 31/665* | (2006.01) | |
| *A61L 24/00* | (2006.01) | |
| *A61L 24/06* | (2006.01) | |
| *A01N 57/32* | (2006.01) | |
| *A61L 27/50* | (2006.01) | |
| *A61L 27/54* | (2006.01) | |
| *A61K 9/14* | (2006.01) | |

(52) U.S. Cl.
CPC ............ *A61L 24/0015* (2013.01); *A01N 57/32* (2013.01); *A61K 9/145* (2013.01); *A61K 31/665* (2013.01); *A61L 24/06* (2013.01); *A61L 27/505* (2013.01); *A61L 27/54* (2013.01); *A61L 2300/406* (2013.01); *A61L 2300/802* (2013.01); *A61L 2430/02* (2013.01)

(58) Field of Classification Search
None
See application file for complete search history.

(56) References Cited

U.S. PATENT DOCUMENTS

| 8,075,907 | B2 | 12/2011 | Kühn et al. | |
|---|---|---|---|---|
| 8,263,123 | B2 * | 9/2012 | Morita .................. | A61K 9/0056 424/464 |
| 2008/0213336 | A1 | 9/2008 | Kühn et al. | |

FOREIGN PATENT DOCUMENTS

| CN | 101987082 A | 3/2011 |
|---|---|---|
| CN | 102784118 A | 11/2012 |
| DE | 10 2008 046 610 A1 | 3/2010 |
| EP | 1 949 918 A2 | 7/2008 |
| WO | 2005/074699 A2 | 8/2005 |

OTHER PUBLICATIONS

Nugent et al.: "Strength of Antimicrobial Bone Cement Decreases with Increased Poragen Fraction"; Clin Orthop Relat Res (2010) 468, pp. 2101-2106.
Walenkamp, "Self-mixed antibiotic bone cement: western countries learn from developing countries"; Acta Orthopaedica 2009, 80 (5), pp. 505-507.
Salehi et al.; "A Daptomycin-Xylitol-loaded Polymethylmethacrylate Bone Cement: How Much Xylitol Should Be Used?"; Clin Orthop Relat Res (2013) 471; pp. 3149-3157.
Beenken et al.; "Use of Xylitol to Enhance the Therapeutic Efficacy of Polymethylmethacrylate-Based Antibiotic Therapy in Treatment of Chronic Osteomyelitis"; Antimicrobial Agents and Chemotherapy, Nov. 2012, vol. 56, No. 11, p. 5839-5844.
European Search Report dated Aug. 6, 2015 in corresponding application.
German Office Action dated Mar. 13, 2015 in corresponding application.
D. Hendlin et al.: "Phosphonomycin a new antibiotic produced by strains of *Streptomyces*"; Science 96 (1969) 122-123.
F. M. Kahan et al.: "The mechanism of action of fosfomycin (phosphonomycin)"; Ann N Y Acad Sci 235 (1974) 364-386.
E. D. Brown et al.: "MurA (MurZ), the enzyme that catalyzes the first committed step in peptidoglycan biosynthesis, is essential in *Escherichia coli*"; J. Bacteriol. 177 (14) (1995) 4194-4197.
W. Graninger et al.: "In vitro activity of fosfomycin against methicillin-susceptible and methicillin-resistant *Staphylococcus aureus*"; Infection 12 (1984) 293-295.
F. Allerberger, et al.: "In-vitro activity of fosfomycin against vancomycin-resistant enterococci"; J Antimicrob Chemother 43 (1999) 211-217.
T. Hara et al.: "Antimicrobial activity of fosfomycin against beta-lactamase-producing methicillin-sensitive *Staphylococcus aureus* and methicillin-sensitive coagulase-negative *staphylococci*"; Jpn J Antibiot 56 (2003) 142-147.
M. E. Falagas et al.: "Fosfomycin for the treatment of multidrug-resistant, including extended-spectrum β-lactamase producing enterobacteriaceae infections: a systematic review"; Lancet Infect Dis 10 (2010) 43-50.

\* cited by examiner

*Primary Examiner* — Heidi Reese
(74) *Attorney, Agent, or Firm* — Norris McLaughlin & Marcus, P.A.

(57) ABSTRACT

The invention relates to a fosfomycin preparation that comprises a) a calcium salt of fosfomycin and b) at least one sugar alcohol having a melting point above 70° C., whereby the weight ratio of sugar alcohol to calcium salt of fosfomycin is at least 0.8. Moreover, the invention proposes a method for producing the fosfomycin preparation and a polymethylmethacrylate bone cement powder that contains the fosfomycin preparation.

12 Claims, No Drawings

FOSFOMYCIN PREPARATION, A METHOD FOR PRODUCING THE PREPARATION, AND A POLYMETHYLMETHACRYLATE BONE CEMENT POWDER CONTAINING THE PREPARATION

This patent application claims priority of German Patent Application No. 10 2014 104 676.8, filed on Apr. 2, 2014, the entire contents of which is incorporated herein by reference.

The invention relates to a fosfomycin preparation, a method for producing the preparation, and a polymethylmethacrylate bone cement powder containing the preparation.

Articular endoprostheses are used extensively and very successfully in a broad range of articular diseases aiming to maintain the mobility of the patients. Unfortunately, a small fraction of the patients suffers infections at the articular endoprostheses and in the surrounding bone tissue and soft tissue. To treat these infections, it is very common to perform a one-stage or two-stage revision of the articular endoprosthesis.

Revision polymethylmethacrylate bone cements containing an antibiotic or two or more antibiotics have proven expedient for permanent mechanical fixation of the revision articular endoprostheses. Said antibiotics protect the revision articular endoprosthesis and the surrounding bone tissue and soft tissue, at least right after the surgery, from renewed microbial colonisation. Aside from individualised admixture of antibiotics by the physician, industrially produced revision polymethylmethacrylate bone cement have proven expedient.

Accordingly, Heraeus Medical GmbH manufactures and distributes the revision polymethylmethacrylate bone cements, Copal® G+C and Copal® G+V. Copal® G+C contains the combination of gentamicin and clindamycin. Copal® G+V contains the combination of gentamicin and vancomycin. The combination of gentamicin and vancomycin is particularly well-suited, thus far, if the infection of the articular endoprosthesis is caused by methicillin-resistant staphylococci (MRSA, MRSE).

However, vancomycin-resistant strains of staphylococci and enterococci have been known for a number of years as well. It is to be expected that these vancomycin-resistant bacteria will assume an increasing role as the causes of joint-associated infections in the near future. Therefore, it makes sense to develop a revision polymethylmethacrylate bone cement that contains at least one antibiotic possessing activity against vancomycin-resistant bacteria. Besides, increasingly problematic gram-negative bacteria also are significant as causes of joint-associated infections. This concerns, in particular, the so-called ESBL strains.

Fosfomycin is an antibiotic with a very broad range of activity. The antibiotic fosfomycin ((2R,3S)-3-methyloxiran-phosphonic acid, CAS 23155-02-4) was discovered in 1969 (D. Hendlin et al.: Phosphonomycin a new antibiotic produced by strains of *Streptomyces*. Science 96 (1969) 122-123.)

Fosfomycin inhibits the bacterial enzyme, MurA (UDP-N-acetylglucosamine-enolpyruvyl-transferase) (F. M. Kahan et al.: The mechanism of action of fosfomycin (phosphonomycin). Ann N Y Acad Sci 235 (1974) 364-386; E. D. Brown et al.: MurA (MurZ), the enzyme that catalyzes the first committed step in peptidoglycan biosynthesis, is essential in *Escherichia coli*. J. Bacteriol. 177 (14) (1995) 4194-4197). It catalyses the first step of murein biosynthesis. In this step, an enolpyruvil moiety based on phosphoenolpyruvate (PEP) is transferred to the hydroxyl group at position 3 of UDP-N-acetylglucosamine. This means that a lactic acid ether is generated at position 3 of UDP-N-acetylglucosamine. The disruption of this step by fosfomycin inhibits the bacterial cell wall synthesis.

Fosfomycin acts bactericidal in susceptible bacteria. Fosfomycin is active against both gram-negative and gram-positive bacteria including methicillin-resistant staphylococci (W. Graninger et al.: In vitro activity of fosfomycin against methicillin-susceptible and methicillin-resistant *Staphylococcus aureus*. Infection 12 (1984) 293-295). Fosfomycin is also efficacious against vancomycin-resistant *Staphylococcus aureus* (VRS) and vancomycin-resistant enterococci (F. Allerberger, I. Klare: In-vitro activity of fosfomycin against vancomycin-resistant enterococci. J Antimicrob Chemother 43 (1999) 211-217; T. Hara et al.: Antimicrobial activity of fosfomycin against beta-lactamase-producing methicillin-sensitive *Staphylococcus aureus* and methicillin-sensitive coagulase-negative staphylococci. Jpn J Antibiot 56 (20013) 142-147). In addition, fosfomycin is also efficacious against ESBL (M. E. Falagas et al.: Fosfomycin for the treatment of multidrug-resistant, including extended-spectrum β-lactamase producing enterobacteriaceae infections: a systematic review. Lancet Infect Dis 10 (2010) 43-50).

For pharmaceutical use, fosfomycin is converted to salts that are sufficiently stable during storage and form aqueous solutions that have a physiologically tolerable pH value. The European Pharmacopoeia describes three fosfomycin salts. These are the monohydrate of the calcium salt of fosfomycin (CAS 26016-98-8), the disodium salt of fosfomycin (CAS 26016-99-9), and trometamol-fosfomycin (CAS 78964-85-9).

The sodium salt and the calcium salt of fosfomycin are extraordinarily hygroscopic. Both salts attract atmospheric humidity and deliquesce in the process. Experiments have shown that these salts, in the dry state, can be integrated into cement powders of polymethylmethacrylate bone cements. However, said cement powders also attract atmospheric humidity during storage on air, upon which the antibiotic particles deliquesce. This can cause the cement powder to clump. For this reason, both of these fosfomycin salts are unsuitable or poorly suitable for industrial production of antibiotic polymethylmethacrylate bone cement powders. Although trometamol-fosfomycin is also somewhat hygroscopic, this is somewhat less pronounced than is the case with the calcium salt and the disodium salt of fosfomycin.

The calcium salt of fosfomycin is particularly interesting for the production of antibiotic polymethylmethacrylate bone cements. Calcium ions are an essential mineral component of the bone. It can therefore be presumed that a polymethylmethacrylate bone cement containing the calcium salt of fosfomycin will be tolerated by the bone tissue. Due to the hygroscopic properties of the calcium salt of fosfomycin, it is basically impossible to easily incorporate said salt into polymethylmethacrylate bone cement powder. Industrial production of polymethylmethacrylate bone cement is basically impossible to implement.

It is the object of the invention to overcome the aforementioned disadvantages of the prior art. Specifically, the invention is to provide a preparation of the calcium salt of fosfomycin that is powdered at room temperature and shows only minimal hygroscopic properties. The preparation is to not deliquesce due to the addition of atmospheric humidity at room temperature and a relative humidity of 50%. Moreover, said preparation is to be present as a free-flowing powdered solid that can be ground without any difficulty, does not attract atmospheric humidity, and does not deliquesce. It is another object of the invention to develop a polymethylmethacrylate bone cement powder that contains the preparation of the calcium salt of fosfomycin and meets the minimal mechanical requirements of ISO 5833 for polymethylmethacrylate bone cements.

Surprisingly, the object of the invention was met by a preparation of the calcium salt of fosfomycin containing a sugar alcohol having a melting point above 70° C.

Therefore, the invention relates to a fosfomycin preparation comprising
  a) a calcium salt of fosfomycin and
  b) at least one sugar alcohol having a melting point above 70° C.,
whereby the weight ratio of sugar alcohol to calcium salt of fosfomycin is at least 0.8.

The invention is based on the surprising finding that mixtures of the calcium salt of fosfomycin and at least one sugar alcohol having a melting point above 70° C. are clearly less, or barely, hygroscopic in contrast to the calcium salt of fosfomycin alone. The mixtures can be stored without difficulty on air at a relative humidity of 50% at room temperature without the preparation deliquescing due to atmospheric humidity being attracted or without the preparation agglomerating into a semi-liquid mass as is the case with the calcium salt of fosfomycin. The fosfomycin preparation according to the invention can be ground without any difficulty and the powder thus obtained shows no pronounced hygroscopic properties and can be handled without difficulty.

Without wishing to be tied to any one theory, it is presumed that the surprising improvement of the hygroscopic behaviour is based on the sugar alcohol interacting with the calcium ions, which markedly reduces the tendency of the calcium ions to attract water.

The preparation according to the invention can be used to produce non-clumping free-flowing polymethylmethacrylate bone cement powders in the presence of non-dried air. As a result, common technical equipment and/or machines can be used without expensive special protective measures against atmospheric humidity to produce a calcium fosfomycin-containing cement powder, e.g. for revision cements.

The invention is explained in detail in the following.

As mentioned above, fosfomycin is (2R,3S)-3-methyloxiranphosphonic acid, CAS 23155-02-4. The calcium salt of fosfomycin usually comprises water of hydration. It is also referred to as the monohydrate of the calcium salt of fosfomycin (CAS 26016-98-8) or calcium-fosfomycin monohydrate. The calcium salt of fosfomycin is commercially available, e.g. from Ecros, Spain. The calcium salt of fosfomycin is a hygroscopic powder.

Any sugar alcohol having a melting point above 70° C. is well-suited as sugar alcohol. Sugar alcohols are also referred to as alditols. One or more sugar alcohols can be used. All stereoisomers or any mixtures of stereoisomers can be used as sugar alcohols. Sugar alcohols are inexpensive and non-objectionable in terms of toxicology.

The sugar alcohol used for the preparation according to the invention preferably is a sugar alcohol having 4, 5 or 6 carbon atoms or a mixture thereof. Suitable examples of a sugar alcohol include erythritol, threitol, xylitol, mannitol, and sorbitol, whereby erythritol, xylitol, and mannitol are particularly preferred.

The weight ratio (b/a) of sugar alcohol (b) to calcium salt of fosfomycin (a) in the fosfomycin preparation according to the invention is at least 0.8, preferably at least 1 and particularly preferably at least 1.5. The weight ratio of sugar alcohol to calcium salt of fosfomycin in the fosfomycin preparation according to the invention usually is no more than 5, preferably no more than 4, and particularly preferably no more than 3.5. However, as a matter of principle, higher weight fractions of sugar alcohol are feasible just as well. Non-hygroscopic powders are obtained in this case as well. However, the amount of non-effective material (sugar alcohol) in the cement thus increases unnecessarily, which usually is not expedient since the mechanical stability is weakened.

The weight ratio of sugar alcohol to calcium salt of fosfomycin preferably is in the range of 0.8 to 5, more preferably of 1 to 4, and particularly preferably of 1.5 to 3.5, whereby the weight ratio of sugar alcohol to calcium salt of fosfomycin particularly preferably is in the range of 2 to 3, e.g. approx. 2 to 1 or approx. 3 to 1.

The fosfomycin preparation according to the invention, in particular, is a solid preparation, i.e. a solid, and preferably is present as a powder. If applicable, it can just as well be present as a granulate. Preferably, the fosfomycin preparation according to the invention is a solidified sugar alcohol melt with calcium salt of fosfomycin dispersed in it, whereby the solidified melt is preferably present in ground or powdered form. If applicable, it can just as well be used in granulated form. Usually, the fosfomycin preparation is a colourless, non-hygroscopic powdered solid.

If applicable, the fosfomycin preparation according to the invention can contain one or more additives. However, the fosfomycin preparation according to the invention preferably consists or essentially consists of the calcium salt of fosfomycin and the sugar alcohol(s).

Preferably, the preparation is produced in simple manner by suspending the calcium salt of fosfomycin in a melt of the at least one sugar alcohol, followed by cooling and grinding the solidified melt. The invention therefore also relates to a method for producing the fosfomycin preparation, comprising the following steps of:
  a) melting the at least one sugar alcohol;
  b) suspending the calcium salt of fosfomycin in the sugar alcohol melt;
  c) cooling the melt after suspending the calcium salt of fosfomycin in it in order to obtain a solidified melt with the calcium salt of fosfomycin dispersed in it; and
  d) grinding the solidified melt in order to obtain a powdered solid.

In step b), the calcium salt of fosfomycin is added into the sugar alcohol melt, in particular, as a solid, preferably as powder. In step c), the melt is preferably being cooled right after the suspension step in order to obtain a solidified melt with the calcium salt of fosfomycin dispersed in it. Usually, the cooling is made to proceed to ambient temperature and/or room temperature. Preferably, the melt is cooled rapidly. For rapid cooling, the customary measures known to a person skilled in the art can be implemented, e.g. external cooling by water or ice water.

The solidified sugar alcohol melt with the calcium salt of fosfomycin dispersed in it is easy to grind in step d), e.g. by hand using a mortar or mill. Grinding results in a colourless, non-hygroscopic powdered solid.

The fosfomycin preparation according to the invention is well-suited for use as an antibiotic agent for powdered compositions, in particular for polymethylmethacrylate bone cement powders. As a result, the difficulties associated with the hygroscopic properties of the calcium salt of fosfomycin can be foregone.

Polymethylmethacrylate bone cements usually are present as two-component systems. The first component usually is a bone cement powder. The bone cement powder is also referred to as polymethylmethacrylate bone cement powder. The second component contains a polymerisable monomer, usually methylmethacrylate, and usually is a liquid. Mixing the two components results in a plastically deformable bone cement dough that hardens (cures) after a certain period of time.

The fosfomycin preparation according to the invention is well-suited, in particular, as antibiotic agent for a bone cement powder for a polymethylmethacrylate bone cement. The invention therefore also relates to a bone cement powder that comprises the fosfomycin preparation according to the invention described above, preferably in the form of a powder.

Preferably, the bone cement powder comprising the fosfomycin preparation according to the invention further contains at least one particulate polymethylmethacrylate or polymethylmethacrylate-co-polymer, a particulate radiopaquer, a radical initiator, and, if applicable, a further antibiotic and/or antiseptic. Preferably, the fraction of the fosfomycin preparation according to the invention present in the bone cement powder is 1 to 20% by weight, based on the total weight of the bone cement powder.

The particulate polymethylmethacrylate or polymethylmethacrylate-co-polymer is, in particular, non-cross-linked polymer and/or copolymer. The particulate polymethylmethacrylate or polymethylmethacrylate-co-polymer preferably is a suspension polymer.

All common particulate radiopaquers can be used as particulate radiopacquer. Pertinent examples include, in particular, zirconium dioxide, barium sulfate, toxicologically non-objectionable heavy metal particles, e.g. tantalum, ferrite, and magnetite, or toxicologically non-objectionable calcium salts.

The purpose of the radical initiator is to initiate the polymerisation of the monomer, usually methylmethacrylate, present in the second component after mixing with the second component. All common radical initiators can be used. Pertinent examples include peroxides and azo-compounds, whereby peroxides and, in particular, dibenzoylperoxide are preferred.

If applicable, the bone cement powder can contain one or more further antibiotics and/or one or more antiseptics. Pertinent examples of further antibiotics that can be present in the bone cement powder, if applicable, include gentamicin, tobramycin, clindamycin, vancomycin, teicoplanin, and daptomycin. Pertinent examples of antiseptics that can be present in the bone cement powder, if applicable, include octenidine dihydrochloride, polyhexanide, calcium peroxide, and carbamide peroxide.

The second component to be mixed with the bone cement powder in order to produce a cement dough can, e.g., be a monomer liquid that is common in this field. A monomer liquid of this type comprises, e.g., methylmethacrylate and a tertiary amine, such as N,N-dimethyl-p-toluidine, as well as a stabiliser, such as p-hydroquinone, and/or a dye, if applicable.

The bone cement powder according to the invention can be used, by mixing with common monomer liquid that is composed, e.g., of methylmethacrylate, N,N-dimethyl-p-toluidine, p-hydroquinone, to produce a plastically deformable bone cement dough, which, after it is cured, meets the requirements of ISO 5833 with regard to the flexural strength being at least 50 MPa, the flexural modulus being at least 1,800 MPa, and the compressive strength being at least 70 MPa.

The bone cement powder containing the fosfomycin preparation according to the invention is particularly well-suited for producing polymethylmethacrylate bone cements for revision purposes, for producing spacers, and for producing local active substance release systems.

Polymethylmethacrylate bone cements for revision purposes shall be understood to mean polymethylmethacrylate bone cements intended for permanent fixation of revision articular endoprostheses used in the scope of a one-stage or two-stage septic revision of infected articular endoprostheses. The term, spacer, shall be understood to mean temporary implants that are inserted, as temporary place-holders, in the scope of the two-stage septic revision of infected articular endoprostheses. The polymethylmethacrylate bone cement powder can just as well be used to produce local active substance release systems, whereby the cement powder is mixed with common mixtures of methylmethacrylate and a tertiary amine, e.g. N,N-dimethyl-p-toluidine, whereby a self-curing cement dough is produced that can be cast or modelled into any shape, whereby mechanically stable form bodies are produced after curing by means of radical polymerisation. These can be used in the scope of local antibiotics therapy. The active substance release systems can be provided to be spherical, bean-shaped, rod-shaped. It is feasible just as well to attach spherical or bean-shaped form bodies to bio-compatible wires.

The invention shall be illustrated in more detail by the following examples without limiting the invention in any way or shape.

EXAMPLES

The following examples use, as calcium salt of fosfomycin, a monohydrate of the calcium salt of fosfomycin that was procured from Ecros, Spain, and is referred to as calcium-fosfomycin monohydrate hereinafter for reasons of simplification.

Example 1

A total of 4.00 g erythritol (melting point 120° C., Sigma-Aldrich) were weighed in a porcelain crucible. The porcelain crucible was then placed on a heating plate, which was at a temperature of 150° C. The erythritol formed a clear melt. A total of 4.00 g calcium-fosfomycin monohydrate were then added to said melt. The calcium-fosfomycin monohydrate was mixed with the melt by vigorous stirring. Then, the mixture was immediately cooled to room temperature. The melt solidified into a colourless solid. Said solid was taken out of the porcelain crucible and ground in a mortar. This produced a colourless powdered solid that could be stored on air without any difficulty without the preparation clumping or deliquescing by attracting atmospheric humidity.

Example 2

A total of 8.00 g erythritol (melting point 120° C., Sigma-Aldrich) were weighed in a porcelain crucible. The porcelain crucible was then placed on a heating plate, which was at a temperature of 150° C. The erythritol formed a clear melt. A total of 4.00 g calcium-fosfomycin monohydrate were then added to said melt. The calcium-fosfomycin monohydrate was mixed with the melt by vigorous stirring. Then, the mixture was immediately cooled to room temperature. The melt solidified into a colourless solid. Said solid was taken out of the porcelain crucible and ground in a mortar. This produced a colourless powdered solid that could be stored on air without any difficulty without the preparation clumping or deliquescing by attracting atmospheric humidity.

Example 3

A total of 12.00 g erythritol (melting point 120° C., Sigma-Aldrich) were weighed in a porcelain crucible. The porcelain crucible was then placed on a heating plate, which was at a temperature of 150° C. The erythritol formed a clear melt. A total of 4.00 g calcium-fosfomycin monohydrate were then added to said melt. The calcium-fosfomycin monohydrate was mixed with the melt by vigorous stirring. Then, the mixture was immediately cooled to room temperature. The melt solidified into a colourless solid. Said solid was taken out of the porcelain crucible and ground in a mortar. This produced a colourless powdered solid that could be stored on air without any difficulty without the preparation clumping or deliquescing by attracting atmospheric humidity.

Example 4

A total of 8.00 g xylitol (melting point 94° C., Sigma-Aldrich) were weighed in a porcelain crucible. The porcelain crucible was then placed on a heating plate, which was at a temperature of 150° C. The xylitol melted and formed a clear melt. A total of 4.00 g calcium-fosfomycin monohydrate were then added to said melt. The calcium-fosfomycin monohydrate was mixed with the melt by vigorous stirring. Then, the mixture was immediately cooled to room temperature. The melt solidified into a colourless solid. Said solid was taken out of the porcelain crucible and ground in a mortar. This produced a colourless powdered solid that could be stored on air without any difficulty without the preparation clumping or deliquescing by attracting atmospheric humidity.

Example 5

A total of 12.0 g xylitol (melting point 94° C., Sigma-Aldrich) were weighed in a porcelain crucible. The porcelain crucible was then placed on a heating plate, which was at a temperature of 150° C. The xylitol formed a clear melt. A total of 4.00 g calcium-fosfomycin monohydrate were then added to said melt. The calcium-fosfomycin monohydrate was mixed with the melt by vigorous stirring. Then, the mixture was immediately cooled to room temperature. The melt solidified into a colourless solid. Said solid was taken out of the porcelain crucible and ground in a mortar. This produced a colourless powdered solid that could be stored on air without any difficulty without the preparation clumping or deliquescing by attracting atmospheric humidity.

Example 6

A total of 8.00 g mannitol (melting point 166° C., Sigma-Aldrich) were weighed in a porcelain crucible. The porcelain crucible was then placed on a heating plate, which was at a temperature of 230° C. The erythritol formed a clear melt. A total of 4.00 g calcium-fosfomycin monohydrate were then added to said melt. The calcium-fosfomycin monohydrate was mixed with the melt by vigorous stirring. Then, the mixture was immediately cooled to room temperature. The melt solidified into a colourless solid. Said solid was taken out of the porcelain crucible and ground in a mortar. This produced a colourless powdered solid that could be stored on air without any difficulty without the preparation clumping or deliquescing by attracting atmospheric humidity.

Polymethylmethacrylate Bone Cement Powder for Examples 7 to 12

In each case, a mixture of 88.53 g particulate polymethylmethacrylate-co-methylacrylate (suspension polymer), 10.00 g zirconium dioxide, and 1.47 g dibenzoylperoxide (75%) (dibenzoylperoxide phlegmatised with 25% by weight water) was produced by grinding using a Turbula mixer.

Example 7

A total of 40.0 g of the polymethylmethacrylate bone cement powder were mixed with 4.00 g of the fosfomycin preparation of example 1. Then 44.0 g of said cement powder were mixed with 20 ml Palacos monomer liquid (mixture containing methylmethacrylate, chlorophyllin E141, N,N-dimethyl-p-toluidine, and p-hydroquinone). This was stirred for 30 seconds. A plastically deformable cement dough was thus produced. Said dough was used to produce strip-shaped test bodies sized 75 mm×10 mm×3.3 mm for testing the flexural strength and flexural modulus in accordance with ISO 5833. In addition, cylindrical test bodies (diameter 6 mm, height 12 mm) for the compressive strength test were produced.

Example 8

A total of 40.00 g of the polymethylmethacrylate bone cement powder were mixed with 4.00 g of the fosfomycin preparation of example 2. A total of 44.0 g of said cement powder were mixed with 20 ml Palacos monomer liquid. This was stirred for 30 seconds. A plastically deformable cement dough was thus produced. Then, test bodies were produced as in example 7.

Example 9

A total of 40.00 g of the polymethylmethacrylate bone cement powder were mixed with 4.00 g of the fosfomycin preparation of example 3. A total of 44.0 g of said cement powder were mixed with 20 ml Palacos monomer liquid. This was stirred for 30 seconds. A plastically deformable cement dough was thus produced. Then, test bodies were produced as in example 7.

Example 10

A total of 40.00 g of the polymethylmethacrylate bone cement powder were mixed with 4.00 g of the fosfomycin preparation of example 4. A total of 44.0 g of said cement powder were mixed with 20 ml Palacos monomer liquid. This was stirred for 30 seconds. A plastically deformable cement dough was thus produced. Then, test bodies were produced as in example 7.

Example 11

A total of 40.00 g of the polymethylmethacrylate bone cement powder were mixed with 4.00 g of the fosfomycin preparation of example 5. A total of 44.0 g of said cement powder were mixed with 20 ml Palacos monomer liquid. This was stirred for 30 seconds. A plastically deformable cement dough was thus produced. Then, test bodies were produced as in example 7.

Example 12

A total of 40.00 g of the polymethylmethacrylate bone cement powder were mixed with 4.00 g of the fosfomycin preparation of example 6. A total of 44.0 g of said cement powder were mixed with 20 ml Palacos monomer liquid. This was stirred for 30 seconds. A plastically deformable cement dough was thus produced. Then, test bodies were produced as in example 7.

Test of the Mechanical Parameters in Accordance with ISO 5833 for Examples 7 to 12

ISO 5833 requires a flexural strength of 50 MPa, a flexural modulus of at least ≥1,800 MPa and compressive strength of 70 MPa. After storage of the test bodies of examples 7 to 12 at 23° C. and a relative humidity of 50° A) for a period of 24 hours, the flexural strength, flexural modulus, and the compressive strength were determined in accordance with ISO 5833. The results show that the mechanical requirements of ISO 5833 with regard to the flexural strength, flexural modulus, and the compressive strength were met by the cements of examples 8-12. The cement of example 7 meets the requirements with regard to the flexural modulus and compressive strength. The flexural strength is at the limit of the requirements of ISO 5833.

| Example | Flexural strength [MPa] | Flexural modulus [MPa] | Compressive strength [MPa] |
| --- | --- | --- | --- |
| 7 | 49.7 ± 2.7 | 3326 ± 61 | 97.5 ± 1.7 |
| 8 | 59.2 ± 3.4 | 3063 ± 140 | 98.5 ± 3.5 |
| 9 | 62.2 ± 2.8 | 3092 ± 68 | 99.5 ± 1.7 |
| 10 | 61.5 ± 2.0 | 2854 ± 50 | 96.8 ± 2.0 |
| 11 | 66.9 ± 2.7 | 3246 ± 120 | 99.4 ± 0.7 |
| 12 | 56.0 ± 1.7 | 3446 ± 86 | 98.6 ± 1.8 |

The invention claimed is:

1. Bone cement powder comprising a fosfomycin preparation comprising:
   a) a calcium salt of fosfomycin; and
   b) at least one sugar alcohol having a melting point above 70° C.;
   whereby the weight ratio of sugar alcohol to calcium salt of fosfomycin is at least 0.8.

2. Bone cement powder according to claim 1, wherein the sugar alcohol comprises 4, 5 or 6 carbon atoms, whereby the sugar alcohol is selected from erythritol, xylitol, and mannitol.

3. Bone cement powder according to claim 1, wherein the weight ratio of sugar alcohol to calcium salt of fosfomycin is at least 1.

4. Bone cement powder according to claim 1, wherein the fosfomycin preparation is a solidified sugar alcohol melt with the calcium salt of fosfomycin dispersed in it.

5. Bone cement powder according to claim 1, wherein the weight ratio of sugar alcohol to calcium salt of fosfomycin is in the range of 0.8 to 5.

6. Bone cement powder according to claim 1, further comprising at least one particulate polymethylmethacrylate or polymethylmethacrylate-co-polymer, a particulate radiopaquer, a radical initiator, and, optionally, a further antibiotic and/or antiseptic.

7. Bone cement powder according to claim 1, wherein the fraction of the fosfomycin preparation present in the bone cement powder is 1 to 20% by weight.

8. Method for producing a bone cement powder according to claim 1, comprising:
   a) melting the at least one sugar alcohol;
   b) suspending the calcium salt of fosfomycin in the sugar alcohol melt while stirring;
   c) cooling the melt with the calcium salt of fosfomycin suspended in it in order to obtain a solidified melt with the calcium salt of fosfomycin dispersed in it;
   d) subjecting the solidified melt to grinding in order to obtain a powdered solid fosfomycin preparation; and
   e) combining the powdered solid fosfomycin preparation with a bone cement powder.

9. Method according to claim 8, which further comprises cooling the melt with the calcium salt of fosfomycin dispersed in it rapidly.

10. A method for one-stage or two-stage septic revision of an infected articular endoprosthesis, said method comprising permanently fixing a revision articular endoprosthesis with a bone cement, wherein the bone cement is a bone cement produced from a bone cement powder according to claim 1.

11. A method for two-stage septic revision of an infected articular endoprosthesis, said method comprising inserting a spacer as a temporary place-holder to replace said infected articular endoprosthesis, wherein the spacer is produced from a bone cement powder according to claim 1.

12. A method for producing a local active substance release system, said method comprising (a) mixing a bone cement powder according to claim 1, methylmethacrylate and a tertiary amine to obtain a self-curing cement dough; (b) casting or modelling the self-curing cement dough to a desired shape; and (c) curing by means of radical polymerization to yield mechanically stable bodies that are suitable for local active substance release.

* * * * *